United States Patent [19]

Haynes

[11] 4,263,301
[45] Apr. 21, 1981

[54] β-PHENYL-β-HYDROXYE-
THYLAMINOALKYLTHEOPHYLLINES AS
INHIBITORS OF BIOSYNTHESIS OF
TRIGLYCERIDES

[75] Inventor: George R. Haynes, Houston, Tex.
[73] Assignee: Shell Oil Company, Houston, Tex.
[21] Appl. No.: 114,781
[22] Filed: Jan. 24, 1980
[51] Int. Cl.³ .............................................. A61K 31/52
[52] U.S. Cl. ..................................................... 424/253
[58] Field of Search ......................................... 424/253
[56] References Cited
U.S. PATENT DOCUMENTS 3,801,578  4/1974  Harsanyi et al. ................. 424/253 X
3,984,413  10/1976  Metz et al. ....................... 424/253 X
4,060,617  11/1977  Credner et al. ....................... 424/253

FOREIGN PATENT DOCUMENTS 2220256  4/1974  France ..................................... 424/253

OTHER PUBLICATIONS

Klingler, Arzneim.-Forschung/Drug Research, 27(1), No. 1a, pp. 4-14, (1977).

Primary Examiner—F. Cacciapaglia, Jr.

[57]  ABSTRACT

Biosynthesis of triglycerides in swine is inhibited by certain β-phenyl-β-hydroxyethylaminoalkyltheophyllines.

4 Claims, No Drawings

β-PHENYL-β-HYDROXYETHYLAMINOALKYL-THEOPHYLLINES AS INHIBITORS OF BIOSYNTHESIS OF TRIGLYCERIDES

DESCRIPTION OF THE INVENTION

It has been found that biosynthesis of triglycerides in swine is inhibited by certain β-phenyl-β-hydroxyethylaminoalkyltheophyllines, of the general formula:

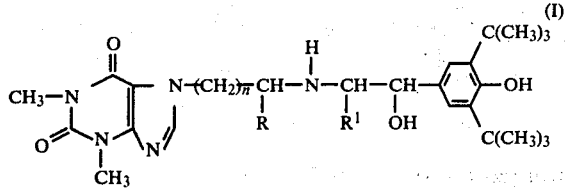

wherein n is one or two, and R and $R^1$ each independently is hydrogen or methyl, and their physiologically acceptable acid addition salts.

These compounds also can be named as β-phenyl-β-hydroxyethylaminoalkyl-3,7-dihydro-1,3-dimethyl-1H-purine-2,6-diones.

Preferred compounds of Formula I are those wherein both of R and $R^1$ are hydrogen.

Suitable salts are those of such acids as acetic, succinic, maleic, fumaric, propionic, citric, lactic, hydrochloric, sulfuric and phosphoric acids. Included in the invention are the individual optically active isomers, and diastereomers, as well as mixtures thereof, that inhibit synthesis of triglycerides.

The compounds of Formula I are known: they, and a method for their preparation, are described in the article by K. H. Klingler, Arzneim.-Forschung/Drug Research, volume 27 (1), No. 1a, pages 4–14 (1977).

The compounds of Formula I have been found to inhibit synthesis of triglycerides in tissues of swine. The manner in which they cause this effect has not been established. Their effectiveness for this purpose has been ascertained by the following procedure.

An enzyme was prepared by homogenizing one gram of slices from pig adipose tissue, each slice being approximately 0.3 mm thick, in one-milliliter portions of a liquid medium (Liquid A). The homogenate then was centrifuged (10,000 g × 15 minutes), and the supernatant phase (the enzyme) was poured through cheesecloth to remove fat that has risen to the top of the centrifuge tubes.

Liquid A had the following composition (in water): 0.15 M potassium chloride, 1 mM ethylenediaminetetracetic acid, 10 mM Hepes (N-2-hydroxyethylpiperazine-N'-2-ethanesulfonic acid), 1 mM DTT (dithiothreitol), pH=7.0.

A solution of the test compound (Liquid B) was prepared: 10 milligrams of test compound plus 0.5 milliliter dimethylsulfoxide (DMSO) plus 1.83 milliliters of glass-distilled water.

A premix (Liquid C) was freshly prepared before each test, from the following components.

| Solutions (in water) | Amount (ml) |
|---|---|
| 1 M Hepes (pH = 7.4) | 3.00 |
| 0.2 M adenosine triphosphate (ATP) (pH = 7.0) | 0.30 |
| 10 mM coenzyme A (pH = 6.6, containing 15 mM DTT) | 0.16 |
| 0.1 M DTT (pH = 7.0) | 0.20 |
| 5% fatty acid-free bovine serum albumin | 0.20 |
| 1 M magnesium chloride | 0.10 |
| Water | 0.44 |
| 20 mM potassium palmitate (kept warm and added to the other components just before use of the mixture) | 0.60 |

0.163 milliter of Liquid B (containing the test compound, or for comparison omitting the test compound) was mixed with 0.1 milliter of Liquid C, 0.05 milliliter of a solution of L-[U-$^{14}$C]glycerol-3-phosphate (containing 5 microcuries of $^{14}$C per milliliter), 0.01 milliliter of 0.8 M potassium phosphate (pH=7.4), 0.07 milliliter of 0.2 M glycerol-3-phosphate (pH=7.4) and 0.047 milliliter of water.

0.25 milliliter of enzyme then was added. The final concentrations of DMSO and test compound were 5% and 1000 micrograms per milliliter, respectively. The mixture was incubated for eight minutes at 37° C. A blank control without enzyme was incubated under the same conditions. Then 3 milliliters of a 1:2 (v/v) mixture of chloroform and methanol was added and thoroughly mixed to terminate the reaction. After 10 minutes, 2 milliliters of chloroform and 1 milliliter of 0.1 N hydrochloric acid were added to the stirred mixture. The mixture was then centrifuged (275 g) for five minutes at room temperature. The top layer of the sample was siphoned off. 2 milliliters of 0.1 N hydrochloric acid in 50% methanol/water was added, the mixture was centrifuged (275 g ) and the top layer was carefully siphoned off. The resulting liquid (the chloroform phase) was transferred to a liquid scintillation vial and air-dried. Ten milliliters of a 2:1 (v/v) mixture of toluene and Triton X-100 containing 0.27% New England Nuclear Omnifluor was added, and the radioactivity was determined in a liquid scintillation counter.

Three replicates (samples of enzyme) were conducted per experiment (per animal). The results were reported as the average of the values obtained from the adipose tissue from two experiments (i.e., two different animals).

The percent inhibition by the test compound compared to the controls (in test compound) was determined.

The results are summarized in the following table.

| Test Compound | Percent Inhibition |
|---|---|
| 7-(2-(2-(3,5-bis-(1,1-dimethylethyl)-4-hydroxyphenyl)-2-hydroxyethylamino)ethyl)-3,7-dihydro-1,3-dimethyl-1H-purine-2,6-dione, hydrochloride | 95 |
| 7-(3-(2-(3,5-bis(1,1-dimethylethyl)-4-hydroxyphenyl)-2-hydroxyethylamino)propyl)-3,7-dihydro-1,3-dimethyl-1H-purine-2,6-dione, hydrochloride | 93 |

The compounds of Formula I can be used to control triglyceride biosynthesis in swine by administering an effective amount of one or a mixture of two or more of the compounds orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the compound needed to inhibit synthesis of the triglycerides will depend upon the particular compound used, and the particular animal being treated. However, in general, satisfactory results are obtained when the compounds are administered in a dosage of from about 1 to about 500 milligrams per kilogram of the animal's body weight. The compound can be administered in a single dose or in a series of doses in the same day, or over a period of days. For any particular animal, a specific dosage regimen should be adjusted according to the individual need, the particular compound(s) used as the inhibitor, and the professional judgment of the person administering or supervising the administration of the inhibitor. It is to be understood that the dosages set forth herein are exemplary only, and that they do not, to any extent, limit the scope or practice of the invention.

I claim:

1. A method for inhibiting biosynthesis of triglycerides in swine which comprises administering, to a pig in need of said treatment, orally or parenterally, an effective amount of a compound of the formula:

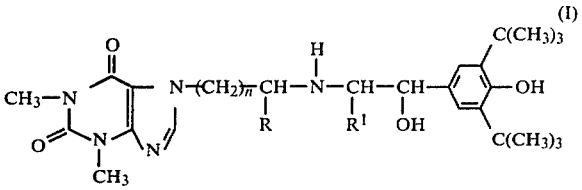

wherein n is one or two, and R and $R^1$ each independently is hydrogen or methyl, and their physiologically acceptable acid addition salts.

2. A method according to claim 1 wherein both of R and $R^1$ are hydrogen.
3. A method according to claim 2 wherein n=1.
4. A method according to claim 2 wherein n=2.

* * * * *